US008781899B2

(12) United States Patent
Edwards et al.

(10) Patent No.: US 8,781,899 B2
(45) Date of Patent: Jul. 15, 2014

(54) ADVERTISING A PHARMACEUTICAL PRODUCT TO A THIRD PARTY

(75) Inventors: Eric Edwards, West Henrietta, NY (US); Christopher Mann, Pittsford, NY (US); Jacqueline Parks, Honeoye Falls, NY (US)

(73) Assignee: Voiceport, LLC, Pittsford, NY (US)

( * ) Notice: Subject to any disclaimer, the term of this patent is extended or adjusted under 35 U.S.C. 154(b) by 2017 days.

(21) Appl. No.: 11/564,286

(22) Filed: Nov. 28, 2006

(65) Prior Publication Data

US 2007/0208945 A1  Sep. 6, 2007

Related U.S. Application Data

(60) Provisional application No. 60/740,177, filed on Nov. 28, 2005, provisional application No. 60/740,182, filed on Nov. 28, 2005.

(51) Int. Cl.
*G06Q 30/00* (2012.01)
*G06Q 30/02* (2012.01)

(52) U.S. Cl.
CPC ........ *G06Q 30/0257* (2013.01); *G06Q 30/0276* (2013.01); *G06Q 30/0271* (2013.01); *G06Q 30/0272* (2013.01)
USPC .................. 705/14.55; 705/14.72; 705/14.67; 705/14.68; 705/14.69

(58) Field of Classification Search
CPC .......... G06Q 30/0257; G06Q 30/0276; G06Q 30/0271; G06Q 30/0272
USPC ........... 705/14.55, 14.72, 14.67, 14.68, 14.69
See application file for complete search history.

(56) References Cited

U.S. PATENT DOCUMENTS

| | | | | |
|---|---|---|---|---|
| 5,090,734 A * | 2/1992 | Dyer et al. | ...................... | 283/67 |
| 5,893,098 A * | 4/1999 | Peters et al. | ................. | 709/200 |
| 6,070,145 A * | 5/2000 | Pinsley et al. | ................ | 705/7.32 |
| 6,151,581 A * | 11/2000 | Kraftson et al. | ................... | 705/3 |
| 6,317,719 B1 * | 11/2001 | Schrier et al. | ..................... | 705/2 |
| 6,477,504 B1 * | 11/2002 | Hamlin et al. | ............... | 705/7.32 |
| 6,807,531 B1 * | 10/2004 | Kanai | ................ | 705/2 |
| 6,826,540 B1 * | 11/2004 | Plantec et al. | ............... | 705/7.32 |
| 6,857,024 B1 * | 2/2005 | Chen et al. | ..................... | 709/231 |
| 7,197,504 B1 * | 3/2007 | Runkler et al. | ................. | 706/45 |
| 7,519,539 B1 * | 4/2009 | Fliess et al. | ................... | 705/301 |
| 8,392,244 B1 * | 3/2013 | O'Halloran | .................. | 705/14.1 |
| 2001/0049621 A1 * | 12/2001 | Raposo | .......................... | 705/10 |
| 2002/0046085 A1 * | 4/2002 | Rochon et al. | .................. | 705/14 |
| 2002/0065683 A1 * | 5/2002 | Pham et al. | ....................... | 705/2 |
| 2002/0128898 A1 * | 9/2002 | Smith et al. | ...................... | 705/10 |
| 2002/0186818 A1 * | 12/2002 | Arnaud et al. | ................ | 378/165 |
| 2003/0028380 A1 * | 2/2003 | Freeland et al. | .............. | 704/260 |
| 2003/0074272 A1 * | 4/2003 | Knegendorf et al. | ........... | 705/26 |
| 2004/0210820 A1 * | 10/2004 | Tarr et al. | ...................... | 715/500 |
| 2005/0075919 A1 * | 4/2005 | Kim | .................. | 705/10 |
| 2005/0081239 A1 * | 4/2005 | Makowski et al. | ............. | 725/35 |
| 2006/0116908 A1 * | 6/2006 | Dew et al. | ......................... | 705/2 |

(Continued)

*Primary Examiner* — Justin M Pats
*Assistant Examiner* — Octavian Rotaru
(74) *Attorney, Agent, or Firm* — Hulsey Calhoun, P.C.; William N. Hulsey, III; Jacob S. Mattis

(57) ABSTRACT

The disclosed subject matter is a method and system for marketing a client's product for an alternative purpose. The information about the alternative purpose of the product is collected and input into an automated system. The method and system then informs third parties about the client's product along with suggested alternative uses.

9 Claims, 6 Drawing Sheets

(56) References Cited

U.S. PATENT DOCUMENTS

| | | | |
|---|---|---|---|
| 2006/0204944 A1* | 9/2006 | Preskill | 434/322 |
| 2007/0038516 A1* | 2/2007 | Apple et al. | 705/14 |
| 2007/0053513 A1* | 3/2007 | Hoffberg | 380/201 |
| 2008/0065471 A1* | 3/2008 | Reynolds et al. | 705/10 |
| 2008/0172214 A1* | 7/2008 | Col et al. | 703/11 |

* cited by examiner

ADVERTISING A PHARMACEUTICAL PRODUCT TO A THIRD PARTY

This application claims the benefit of priority to U.S. Provisional Patent Application No. 60/740,177 entitled "PERSONA-DRIVEN METHOD FOR COMPILING ADVERTISING DATA USING VOICE INTERFACE SYSTEM," by Eric Edwards filed on Nov. 28, 2005, and is incorporated herein by reference as if fully set forth herein. This application also claims the benefit of priority to U.S. Provisional Patent Application No. 60/740,182 entitled "METHOD FOR COMPILING ADVERTISING DATA USING VOICE INTERFACE SYSTEM," by Eric Edwards filed on Nov. 28, 2005, and is incorporated herein by reference as if fully set forth herein.

This application incorporates by reference the co-pending patent application entitled "AUTOMATED METHOD, SYSTEM, AND PROGRAM FOR AIDING IN PRODUCT ADVERTISEMENT", by Eric Edwards filed on Nov. 28, 2006, and is incorporated herein by reference as if fully set forth herein.

This application incorporates by reference the co-pending patent application entitled "AUTOMATED METHOD, SYSTEM, AND PROGRAM FOR GENERATION OF AN AUDIO SURVEY", by Eric Edwards filed on Nov. 28, 2006, and is incorporated herein by reference as if fully set forth herein.

This application incorporates by reference the co-pending patent application entitled "AUTOMATED METHOD, SYSTEM, AND PROGRAM FOR AIDING IN PRODUCT COMPLIANCE AND ADHERENCE", by Eric Edwards filed on Nov. 28, 2006, and is incorporated herein by reference as if fully set forth herein.

TECHNICAL FIELD OF THE INVENTION

The disclosed subject matter relates to strategically marketing a product. More specifically, the disclosed subject matter deals with informing a third party about potential alternative uses of a client's product.

BACKGROUND OF THE INVENTION

The disclosed subject matter is a method and system for marketing a client's product for an alternative purpose. The information about the alternative purpose of the product is collected and input into an automated system. The method and system then informs third parties about the client's product along with suggested alternative uses.

Once a product is released to the market, it invariable becomes associated only with the initial purpose. As time passes, new applications for existing products are discovered. An example could be a medication that was meant to fight cancer could have unexpected anti-viral properties.

When a new use for an old product is discovered, a research period follows where others use the product to see if the results can be duplicated. Clients cannot necessarily claim the product will provide specific results, but suggestions are allowable. Clients are interested in seeing if these new properties could make their product more profitable.

In order to make third parties purchase the product for an alternative purpose, the client needs to inform the third party not only of what the alternate purpose is, but also they need to persuade them to use the product. This leads to a tension. If the advertisement is too brief, then it might not be persuasive. If the advertisement is too detailed, then it could become cost prohibitive.

A common method for targeted advertisement involves the use of direct mailings. The client takes a list of third parties and sends them an advertisement for a product. These advertisements range from simple cards alerting the customer to the product's existence to complete information packages on the product. The more complex the written material, the more expensive the advertisement.

Another form of targeted advertisement comes from an in person visit by a client's representative. This allows one-on-one personal interaction between the third party and the client. Usually, restrictions on the time of both parties are involved, making these visits brief. A client's representative might have an entire catalogue of products to tell the third party about, but only have time to give his presentation on one or two high profile products.

As these two forms of targeted advertisement demonstrate, clients have a difficult time giving all the relevant information on the product to third parties in a cost effective manner. Both forms have serious restrictions, either by quality of information relayed or amount of time available. There exists a need to follow up advertisement for use at the third party's convenience that can persuasively communicate the need to purchase the product.

Communication between the client and the third party helps to address this inefficiency of advertisement. Obstacles to communication include identifying the third parties and establishing a mechanism to communicate between the client and the third party. This presents a difficulty without a pre-existing relationship between the client and the third party. Without some form of initial contact, advertisement is not possible.

Telephone calls offer a considerable advantage to other modes of communication such as direct mail or in person solicitation. Use of the telephone does offer some drawbacks. Telephone calls take a large staff to make the number of calls necessary to contact all the third parties. Companies could have employees make these calls, but those employees could perform other needed duties. The client could contract the responsibility to call centers, but that becomes expensive. This commitment of resources makes telephone calls prohibitive for all but large companies to make follow up calls. Even large companies might find it economical to use telephone calls only on high value items.

The disclosed subject matter involves marketing a client's product for alternative purposes to third parties. The client defines the information to communicate to the third parties. Said information is entered into an automated system which third parties are able to contact at their discretion. When the third party contacts the system, the system relays the advertisement to the third party.

SUMMARY OF THE INVENTION

The method and system illustrated and described herein have several features, no single one of which is solely responsible for its desirable attributes. Without limiting the scope as expressed by the description that follows, its more prominent features will now be discussed briefly. After considering this discussion, and particularly after reading the section entitled "DETAILED DESCRIPTION OF THE ILLUSTRATIVE EMBODIMENTS" one will understand how the features of the disclosed subject matter provide for the analysis of source code.

The disclosed subject matter provides a method and system for marketing a client's product for an alternative purpose. The information about the alternative purpose of the product is collected and input into an automated system. The method and system then informs third parties about the client's product along with suggested alternative uses.

The first thing that accomplished is the establishing the alternative information for the product. When a product is initially marketed, there is a primary purpose. After use, a secondary use for the product may be discovered. This information is collected by the client and used for marketing the product for alternative uses.

While the present disclosed subject matter can be applied to numerous applications, this application will illustrate the patent as is applies to the pharmaceutical industry as an example. The disclosed subject matter will provide a service of advertisement calls, as directed by the client who manufactures the product for the third party for the alternative use of the product.

A component of the disclosed subject matter involves defining the product information to communicate to third parties. The disclosed subject matter collects the information in several ways. One method involves the client interacting with an automated system. The method and system would determine how to categorize the product. The method and system would ask the client a series of questions to determine the content of the advertisement. In this example, the method and system would be defined as a pharmaceutical. The basis of the following questions comes from commonly asked questions involved advertisements in the pharmaceutical field.

Alternatively, a personal service agent from the service provider can collect advertisement information to craft a unique advertisement. Customization allows the client greater flexibility in the service. Other alternatives include the client creating their own advertisements and having the service provider simply provide the delivery vehicle.

Upon establishing the content of the advertisements the system processes the information into an audio advertisement with a particular persona. An example would include a stereotypical mechanic with perhaps some garage sounds in the background if the product deals with automotive issues. Another example would use a nurse at a hospital asking health related questions, as in the case of a pharmaceutical product. There would be no limit to the number of personas available. Other alternatives allow the voice used in the calls to come from a particular voice actor as opposed to a standard voice offered by the service provider.

Now that the advertisement is created, the applicable third parties need to contact the service provider to receive the advertisement. The third party can receive the contact information in any possible format. Available choices include a personal contact from a sales representative or through direct mail to give the third parties the contact information for the service provider.

Once the third party contacts the service provider, there are three possibilities in the current embodiment. First, the service provider number called might only have one product associated with it. In that case, the advertisement will give all the applicable information. Secondly, the service provider could advertise more than one product available at that contact number, but the specific advertisement is selected by name or number. The applicable information is dispensed when selected.

A third option is for the advertisements will be interactive. The third party will call the number and answer a series of questions. Answers to these questions determine the third party's needs. These questions will narrow in scope until the third party's needs can be defined in terms of the client's product.

The questions can also help determine a third party's needs in term of products not yet available. This gives the client access to a survey of knowledge that suggests what products third parties would in purchase in the future.

Once the third party's needs are defined in terms of a client's product, the advertisement begins. The applicable information is given to the third party. The third party can order samples of the product for use as applicable.

A factor for consideration when generating the advertisements is the length of the call. The disclosed subject matter will approximate how long each call will take. This could be a relevant factor for cost purposes or for optimum use of the service. One embodiment of the disclosed subject matter offers the service by charging per minute of phone time used in the service. The client might want to consider the trade off of using a more calls with shorter advertisements or more calls with longer advertisements.

BRIEF DESCRIPTION OF DRAWINGS

The accompanying drawings, which are incorporated in and constitute a part of this specification, illustrate several embodiments of the invention and together with the description, serve to explain the principles of the invention.

DETAILED DESCRIPTION OF PREFERRED EMBODIMENTS

Figure 1:
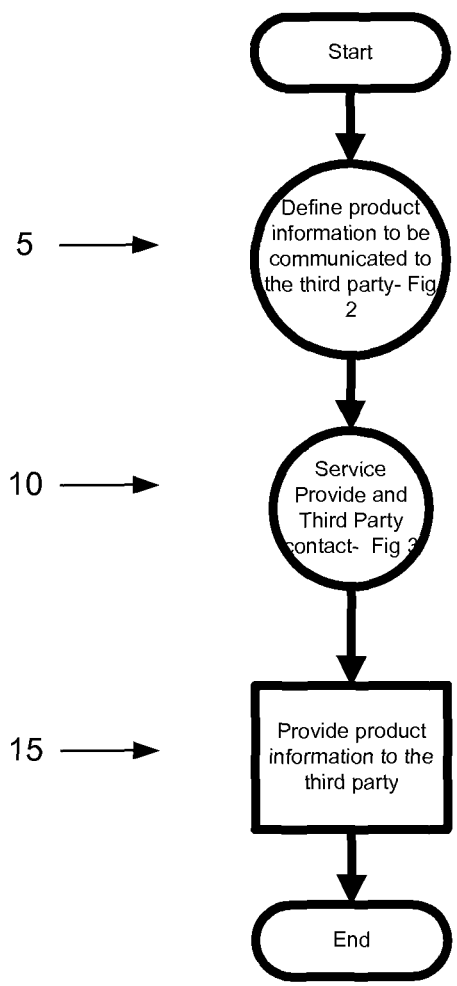
FIG. 1 presents a general overview of the disclosed subject matter. The information is collected by the service provider from the client. The service provider then receives third party contact information. The service provider gives the third party information on the alternative uses of product.
Figure 2:
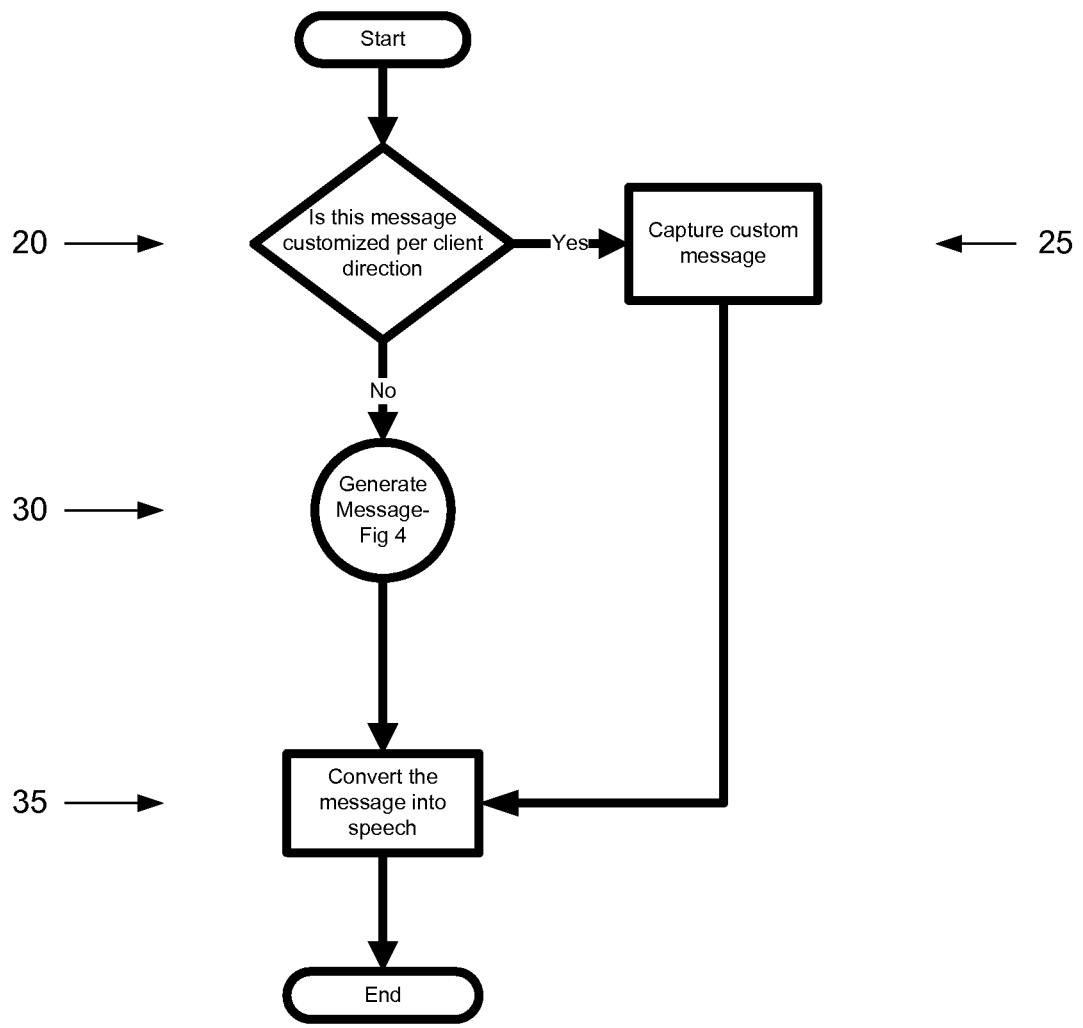
FIG. 2 shows the mechanics of using an automated system for advertisement generation. The information is collected by the service provider from the client and converted into an automated advertisement of an appropriate type.
Figure 3:
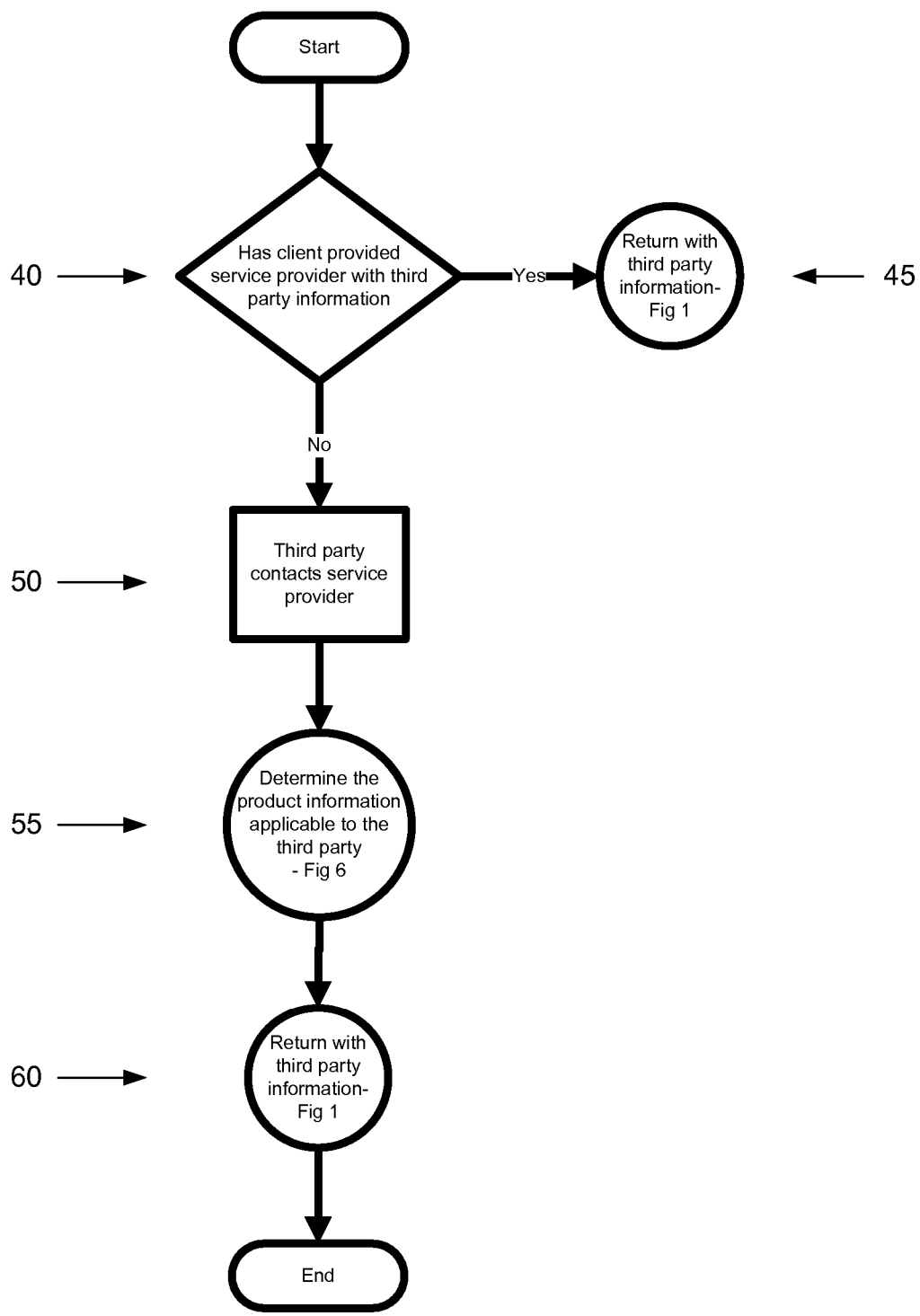
FIG. 3 depicts how the service provider receives the third party contact information.
Figure 4:
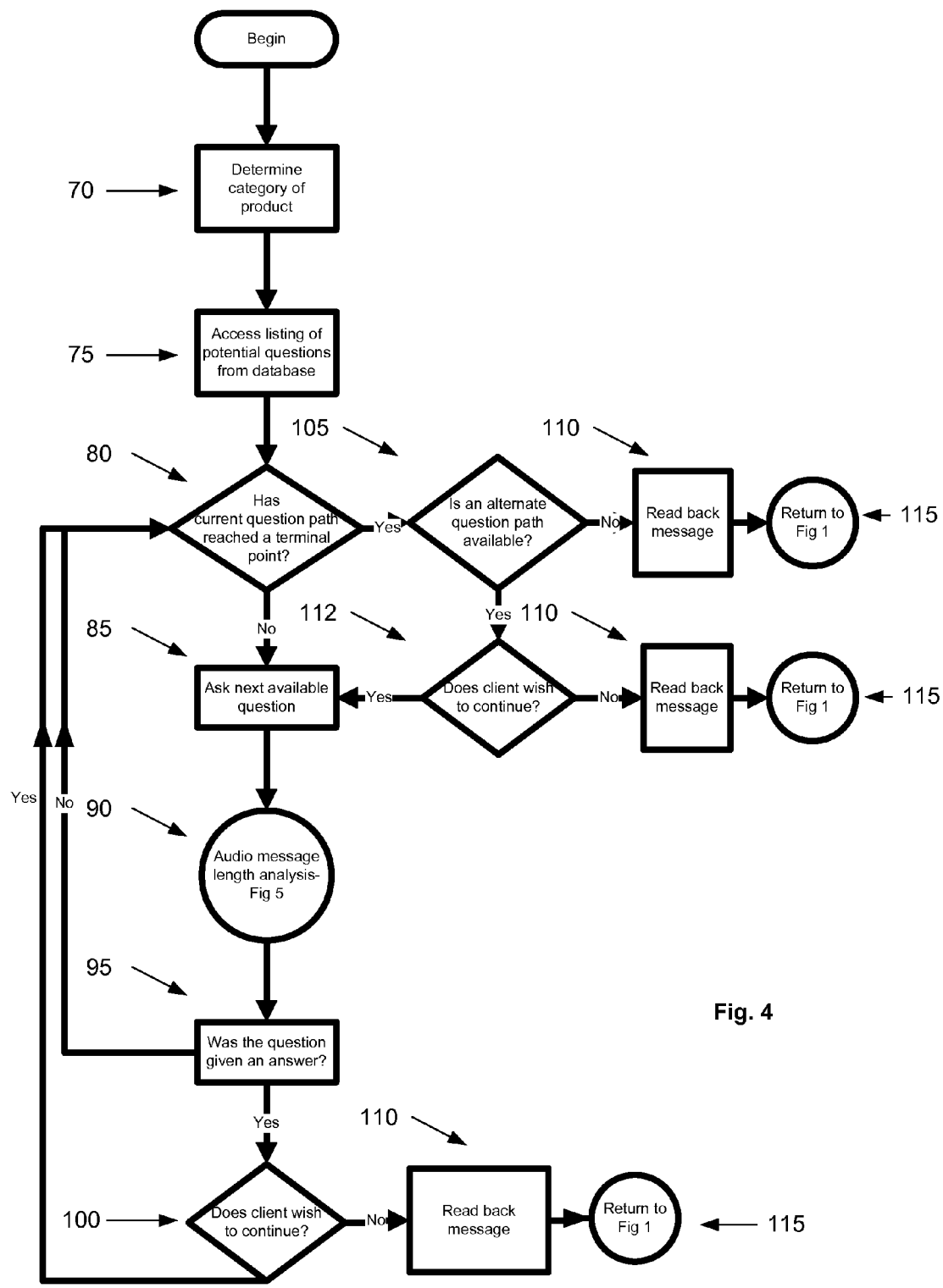
FIG. 4 is an algorithm useful for generating the advertisements.
Figure 5:
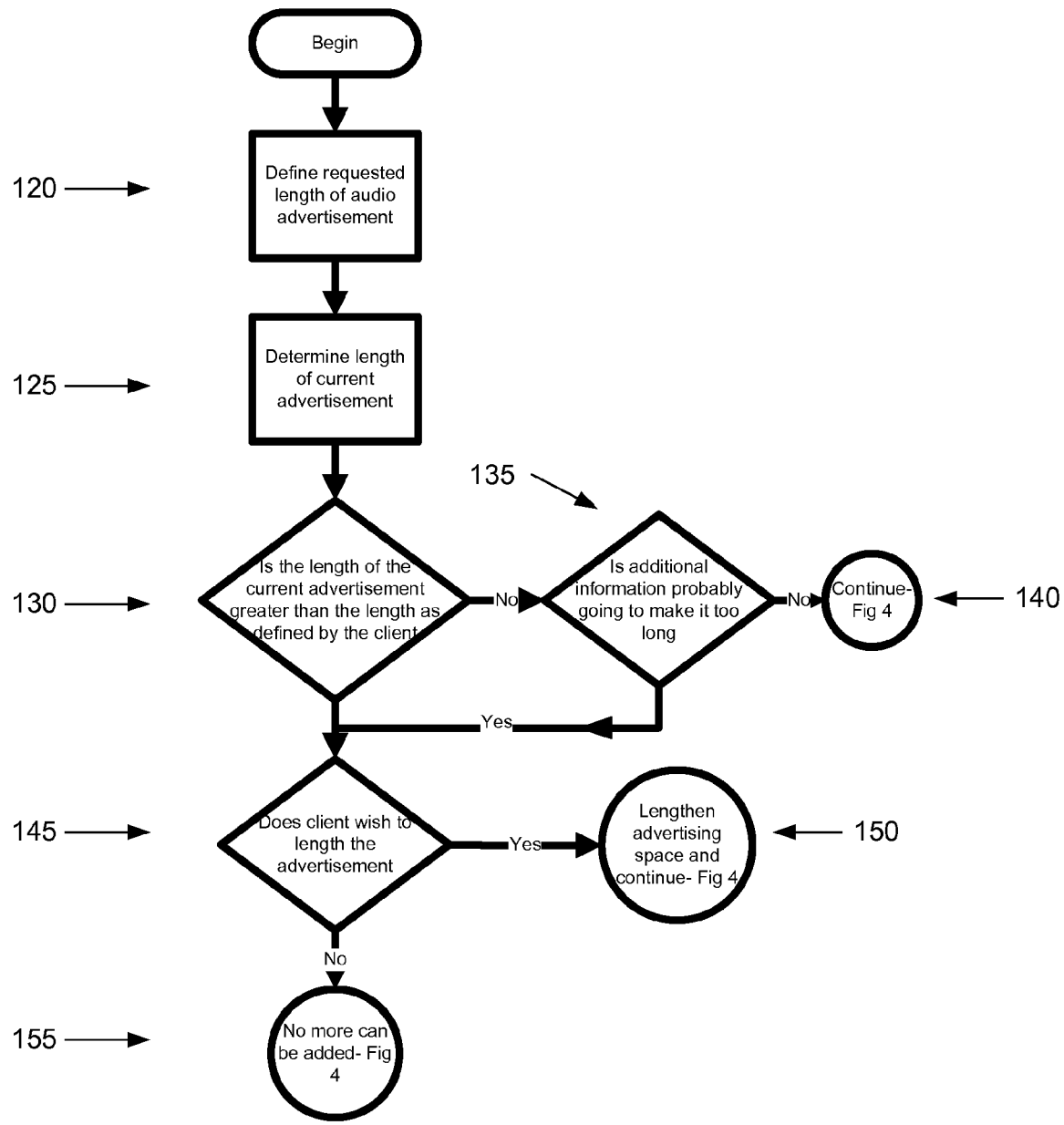
FIG. 5 provides an audio length analysis algorithm, for use in one embodiment where advertisement length is a factor of concern.
Figure 6:
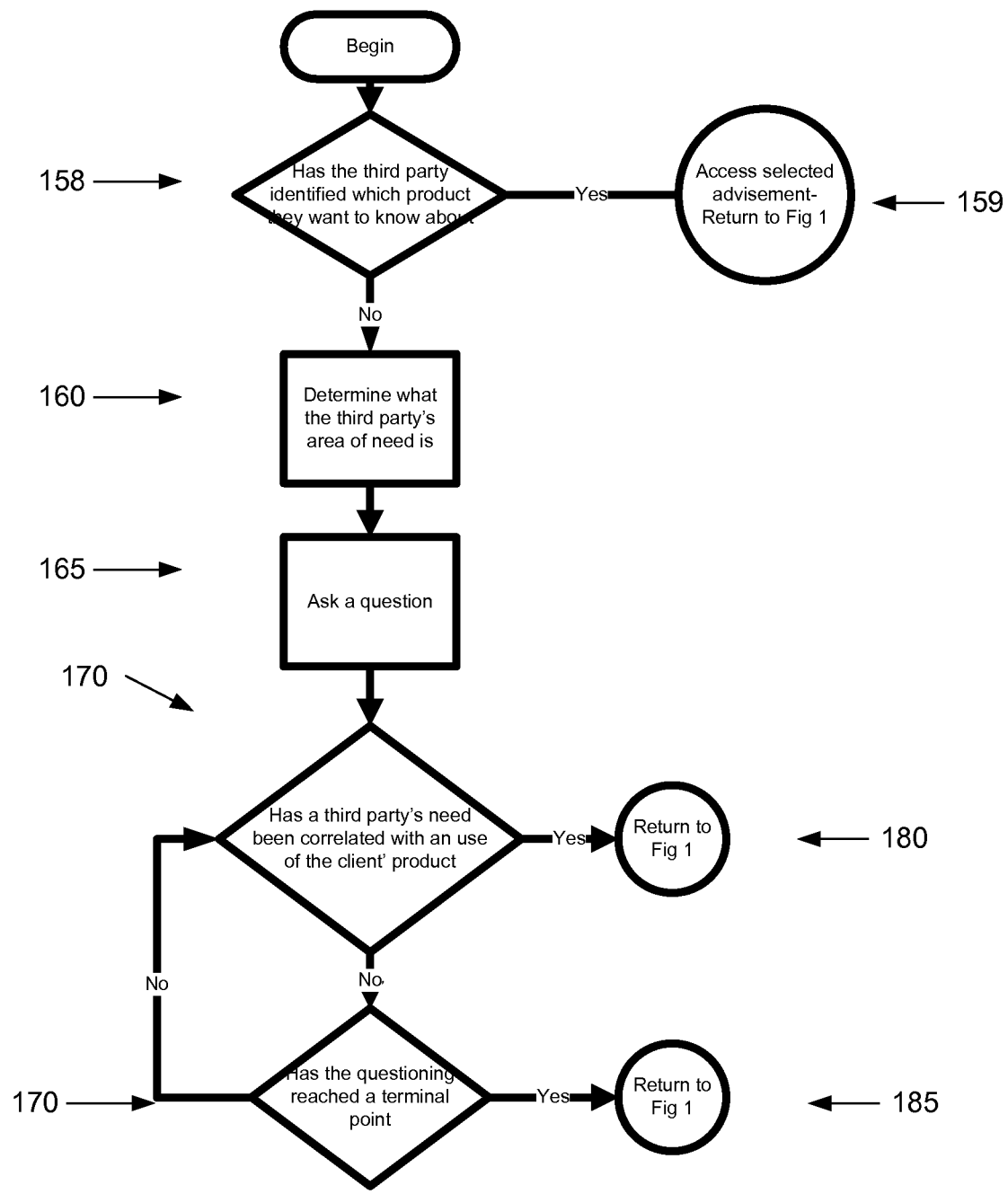
FIG. 6 shows the process of using third party input to determine the appropriate advertisement to present to the third party.

The disclosed subject matter is a method and system for marketing a client's product for an alternative purpose. The information about the alternative purpose of the product is collected and input into an automated system. The method and system then informs third parties about the client's product along with suggested alternative uses.

Although described with particular reference to a systems environment, the claimed subject matter can be implemented in a plurality of information technology (IT) systems. Those with skill in the electronic telecommunications arts will recognize that the disclosed embodiments may be realized in ways in addition to those specific examples described below. In addition, the methods of the disclosed subject matter can be implemented using a variety of combinations of software and hardware. The hardware portion can be implemented using specialized logic; the software portion can be stored in a memory and executed by a suitable instruction execution system such as a microprocessor, PC or mainframe.

All references, including publications, patent applications, and patents, cited herein are hereby incorporated by reference to the same extent as if each reference were individually and specifically indicated to be incorporated by reference and were set forth in its entirety herein.

In the context of this document, a "memory" can be any means that contains stores, communicates, propagates, or transports the program and/or data for use by or in conjunction with an instruction execution system, apparatus or device. Memory, recording medium and data store can be, but are not limited to, an electronic, magnetic, optical, electromagnetic, infrared or semiconductor system, apparatus or device. Memory, recording medium and data store also includes, but is not limited to, for example the following: a portable computer diskette, a random access memory (RAM), a read-only memory (ROM), an erasable programmable read-only memory (EPROM or flash memory), and a portable compact disk read-only memory or another suitable medium upon which a program and/or data may be stored.

The disclosed subject matter may be described in the general context of computer-executable instructions, such as program modules, being executed by a computer. Generally, program modules include routines, programs, objects, components, data structures, etc. that performs particular tasks or implement particular abstract data types. The disclosed subject matter may also be practiced in distributed computing environments wherein tasks are performed by remote processing devices that are linked through a communications network. In a distributed computing environment, program modules may be located in local and/or remote computer storage media including memory storage devices.

Preferred embodiments of this disclosed subject matter are described herein, including the best mode known to the inventors for carrying out the disclosed subject matter. Variations of those preferred embodiments may become apparent to those of ordinary skill in the art upon reading the foregoing description. The inventors expect skilled artisans to employ such variations as appropriate, and the inventors intend for the disclosed subject matter to be practiced otherwise than as specifically described herein. Accordingly, this disclosed subject matter includes all modifications and equivalents of the subject matter recited in the claims appended hereto as permitted by applicable law. Moreover, any combination of the above-described elements in all possible variations thereof is encompassed by the disclosed subject matter unless otherwise indicated herein or otherwise clearly contradicted by context.

Although the present disclosed subject matter has been described in detail herein with reference to the illustrative embodiments, it should be understood that the description is by way of example only and is not to be construed in a limiting sense. It is to be further understood, therefore, that numerous changes in the details of the embodiments of this disclosed subject matter and additional embodiments of this disclosed subject matter will be apparent to, and may be made by, persons of ordinary skill in the art having reference to this description. It is contemplated that all such changes and additional embodiments are within the spirit and true scope of this disclosed subject matter as claimed below.

The disclosed subject matter generates a series of audio messages for clients to communicate with third parties for strategic advertisement purposes. The messages are used to inform third parties of alternative uses for the client's product. The disclosed subject matter incorporates certain rules and patterns that have been observed in the structure of information communicated to third parties by clients with additional intelligence from external sources of sales-item data. This methodology provides the algorithmic basis of the advertisement generation process along with the advertisements themselves. The current disclosed subject matter utilizes state of the art voice user interface techniques to provide a comfortable and intuitive interaction with the client or third party. Although the current disclosed subject matter may find a use for any product or service that would benefit from such contact, the exemplary discussion herein will focus on strategic marketing calls in the pharmaceutical industry.

The disclosed subject matter is a method and system for marketing a client's product for an alternative purpose. The information about the alternative purpose of the product is collected and input into an automated system. The method and system then informs third parties about the client's product along with suggested alternative uses. The third party can receive the information from any source, including telephone and web based systems. For example purposes, audio input generation will be used to create the message, while alternatives such as a web based format are available. For example purposes, communication with third parties can use any medium, including telephone and web based systems.

Products become associated with their primary purpose from the moment they enter the marketplace. Over time, clients who manufacture a product may learn of alternative uses for a product. Some of these alternate uses are closely related to the primary purpose. Others are totally different from the original purpose of the product. These alternative uses generally do not enter the public knowledge unless the client makes these uses known. In some instances, these are not clear cut issues of an alternative use. The presentation might not say a product can perform a specific task, but there is evidence to suggest the effect is possible when used with the product. Clients have a need to get this information to third parties to broaden the scope and appeal of the client's product.

The impetus for the third parties to call the service provider can come from any source. Direct mail provides an example of targeting the intended third parties. Direct mail has long been a traditional method of mass advertisement. The economic aspects have been in tension with the level of information disclosed. If a direct mail advisement is too informative, it might be too expensive and not return sufficient results for the effort. Conversely, interested third parties might not have their interest piqued enough to buy the product with a sparse direct mailing. Using this disclosed subject matter, a direct mailing only has to give basic information and invites the third party to follow up with a phone call to the service provider. The service provider then provides the third party the pre generated advertisement. The same contact information communication can be made available through catalogs.

Another way to inform the third party about the advertisement contact information comes from the customer service representatives of the client. When a customer service representative solicits sales through in person visits to prospective third parties, there is usually a very limited amount of time to communicate all the relevant information about a product. The representative might have a multitude of products to sell, but only have enough time to talk about one or two. The service provider can leave a small pamphlet with the third party and instruct them about other products available and how to make contact.

In the example used in this description, the embodiment would involve the product manufacturer being a client of a service provider. Alternatively, the service can be provided by the company who want the calls made by an in-house department. Moreover, the client and the service provider can be one and the same.

The system defines the information to communicate to third parties 5. The disclosed subject matter uses an algorithm to generate such information from the client or the client can directly create the information.

Once the client's advertisement is generated in this example, the third party contacts the service provider 10. The advertisements can then be provided to third parties 15.

An aspect used in some embodiments of the disclosed subject matter to generate the questions and responses to aid in advertising development comes from the use of a database. The database contains information on what the typical client advertisements tell a third party. This database can contain information for a plurality of possible products. The data base also contains a bank of automated input promotes and outputs tat the client can dynamically control in the message advertisement generation.

An aspect used in some embodiments of the disclosed subject matter to generate the questions and responses to aid in advertising development comes from the use of a database. The database contains information on what the typical client advertisements tell a third party. This database can contain information for a plurality of possible products. The data base also contains a bank of automated input promotes and outputs tat the client can dynamically control in the message advertisement generation.

An alternative embodiment allows the client to customize their advertisements by directly providing the service provider with exactly what the client wants the advertisements to communicate without use of the database. The alternative would allow the client the ability to select exactly what they want the advertisements to say. Another alternative available to the client would use personal contact with the service provider. This would allow a collaborative process where both parties come up with a particular set of inputs and outputs for the advertisements. If the client chooses a customized advertisement 20, the advertisement generated by this customized process would be the one used in the system 25. When the customized advertisement processes in the system, it will be converted into an audio message 35.

Otherwise, the service has a list of standard questions and prompts available to aid in message generation. These questions come from a plurality of knowledge bases that have the information needed for the advertisements. As the disclosed subject matter begins, the client receives a query for basic details about the product they are selling. In this example, the category would be something similar to 'medication'. The product classification returns a series of relevant and appropriate prompts, which ask the client to select from this list of the product's criteria based on the classification. The prompts over the telephone system are designed to be conversational and direct, and therefore will elicit responses that are natural to the caller and, likely to be recognized by the system. Alternatively, some responses accept input on the telephone keypad.

If the information used in advertisement comes from a standardized system as opposed to a custom one, the system then generates the advertisement per the embodiment 30. Once all of the information is collected, the system converts the information into the advertisement in audio format 35. The audio format takes on one of a number of personas. The persona used for the advertisement relates to the type of information being communicated. These personas suggest attributes of the speaker that foster creditability in what the advertisement says. Examples include a nurse dispensing medical information, a mechanic talking about a car, a lawyer talking about legal issues, or a pollster asking about how a person plans on voting. Optional sounds include background noises, such as the sound of a hospital in the background for a nurse, or sounds of a garage for a mechanic.

An alternative to the use of a particular persona would be the use of a specified voice actor. This could allow more customization to the client.

The disclosed subject matter then makes contact with third parties. In some embodiments, the client might already have the applicable third party contact information and have provided it to the service provider 40. If so, no more data collection is needed 45. In the example used for illustrative purpose, the service provider does not start with the third party's contact information. In this context, the third party would have to initiate contact with the service provider in order for the service provider to recite the advertisement 50. When the third party makes contact with the service provider, the service provider determines the applicable advertisement to give the third party 55. This advertisement goes to the applicable areas for commutation with the client 60.

When generating the advertisement, the system approaches the information collection for the advertisement in a predetermined manner. The following example will describe a possible algorithm used to collect information from the client. These bullets denote the information that is initially collected from the client to determine the proper categorization 70:

Type of product (Medication)
Type of medication (allergy, heart)
Sub-classification of medication ("decongestant, fever reducer")
Type of medication alternative use (anti-viral, dermatological)
Sub classification of medication alternative use Next, the initially collected information is used to select a capture profile specific to the product. The capture profile consists of a series of capture items that are presented to the caller in sequence to collect additional information about the product. Examples of capture items are 75:

Medication Name
Alternative reason to take the medication
Recommended dosage
Recommended schedule
Notes
Warnings The general algorithm repeats until a termination condition is met. Answers to questions drive subsequent questions to obtain applicable details from the client. The system will also look to see if a question on the list that has not been asked 80. If so, then the system will present the question to the client 85. After the question is asked, the system then analyzes the entire advertisement for audio advertisement length 90. If no answer to the question was given, the system goes to the next question 95. If the client does not wish to continue with the questions, the process completes and the advertisement generates 100. Once a path of questions has been exhausted, the system looks to see if an alternate path of questioning exists 105. If there is no available alternate path, the system reads back the advertisement at that time and generates the advertisement 110. When an alternate path exists, the system asks if the client wishes to continue 112. If so, the system continues with the new question list 110. If not, the system generates the advertisement 110. When the advertisement generation ends, the result is returned back to the relevant portion of the system 115.

The system confirms with the client every piece of information. Failure to confirm or collect a piece of information (for example, repeatedly failing to recognize their last name) results in the caller being transferred to an agent or another alternate based on the embodiment.

An optional aspect of the disclosed subject matter relates to the cost of the service. Some embodiments of the service give the client the option to limit the cost of the service provided by making the call costs falls within a set price boundary 120 in embodiments that charge for the service per the amount of time for each detriment. In doing so, the system will define the amount of time that is applicable to the cost the client wants to spend. This can be used to determine if the advertisement can be lengthened or needs to be reduced.

The system calculates audio advertisement length by use of an algorithm, converting the advertisement into audio format, or other method to those known in the art to determine the resulting advertisement length 125. Based on the returned length of the advertisement, the system will do one of the following:

Check the length of the advertisement and see if it is within the amount paid for 130.

If the most recently added item has raised the price for the advertisement notify the client that the item does not fit 145. Read the advertisement text back and query if they would like to include the most recent item and possibly more in the advertisement and raise the limit on the price per call. If they select more 150, then the process continues. If they choose not to purchase more time per call, then the advisement is concluded 155.

If there is likely additional time available at the current price quoted initially 135 move on to the next capture item 140.

If the advertisement does not likely have additional time at the current price 135, read the advertisement text and current price back to the customer and query if they would like to include more in the advertisement and raise the limit on the price of the call 145.

The algorithm continues until the content of the advertisement meets the client's requirements or all capture items have been presented. The system reads the advertisement back to the client for verification.

The system confirms with the client every piece of information whether it already exists or is collected new from the caller (in the case of incorrect or no information). Failure to confirm or collect a piece of information (for example, repeatedly fails to recognize their last name) results in the caller being transferred to an agent or another alternate based on the program.

When third parties call the service provider, there are several possibilities as to how the third party will access the advertisement they are looking for. The phone number called may relate to one specific product only. In that instance, the advertisement begins automatically. In an alternate version, there multiple products might have the same contact information. The third party would have to select which product they want to receive information about.

Different embodiments approach the information to disclose in different ways. If the system receives a prompt to direct the third party to a specific advertisements 158, then the service provider access the product advertisement 159. Another alternative for advertisement occurs when the third party does not call about a specific product, but calling to see if a client has a product that suits their needs. The service could take the information that was collected from the client about the product and use an algorithm to see if the client has a product that meets the needs of the third party, accessing a database containing information on a client's product 160. The service provider asks the third party a series of questions 165. If the answer suggests a client product 170, then that product is suggested 180. If a product does not meet the third party's needs, then the system looks to see if there are other possible products available 175. If there are no more available products, then the system returns no value 185. If the system can find other questions, it will repeat the process until the options are exhausted or there is a defined product 175.

Another option for the system allows for the capture of billing information. The system checks the customer database for a matching account using the client's name and number. If there is an associated account then the address in the account is confirmed with the caller. Failure to confirm the existing account address will cause the caller to go to an agent. If there is no account then the system collects the caller's address from the caller and creates a new account. In both cases, the advertisement is saved.

If there is no account and collecting the address for the new account fails then a new account is made with the unknown fields marked as incomplete and the advertisement is saved. The caller is then transferred to an agent. During the transfer, the agent is informed (via whisper) that the advertisement has been saved but the name and address fields are incomplete.

The service provider also collects information from the third parties for use in real time analysis for the client. The client can ask the service provider for information to evaluate sales and break the information down by region, specialty, or any other measurable criteria. The information collected can suggest what products clients are interested in purchasing.

An additional option to add to the advertisement is the ability to automatically mail a sample of the product to the third party. Using this option, the service provider asks the third party if third party would like a sample of the product. If the third party agrees, then the service provider collects the third party's shipping information. The service provider arranges for the sample shipping. This can be accomplished in any way agreed upon between the service provider and the client. The client can receive a listing from the service provider and ship to the third party. Alternately, the service provider can have a stock of samples available and ship them to the third party without any interaction from the client.

The disclosed subject matter described herein is a fundamentally novel method and system. By facilitating the collection of information to communicate to third parties on behalf of clients, a service provider can aid a client in informing third parties about the client's product. Following a standardized algorithm, the advertisements are generated in a manner that facilitates easy communication in a creditable manner over a communications medium to the third parties.

Various changes and modification to the embodiments herein chose for the purposes of illustration will readily occur to those skilled in the art. To the extent that such modifications and variations do not depart form the spirit of the invention, they are intended to be included within the scope thereof which is assessed only by fair interpretation of the following claims.

What is claimed is:

1. A computer implemented method for advertising a pharmaceutical product of a client to a third party, comprising:
    defining advertising information of an audio advertisement for the pharmaceutical product by:
        collecting information from the client to determine categorization of the pharmaceutical product according to: a type of medication, a use for at least one medical condition, an alternative use for at least one other medical condition and additional information consisting at least four of: a name of the pharmaceutical product, an alternative reason to use the pharmaceutical product, a recommended dosage of the pharmaceutical product, a recommended schedule of the pharmaceutical product, notes of the pharmaceutical product, and warnings of the pharmaceutical product, identifying, based on the collected information, a length of time of the audio advertisement for the pharmaceutical product according to a per-minute advertisement price the client spends on the audio advertisement, determining when the additional information to be included in the audio advertisement exceeds the length of time of the audio advertisement according to the per-minute advertisement price, and, in response to said determining, lengthening the length of time of the audio advertisement when the client raises the per-minute advertisement price in response to the additional information exceeding the length of time of the audio advertisement, and excluding the additional information when the client does not raise the audio advertisement per-minute price in response to the additional information exceeding the length of time of the audio advertisement;

receiving a request from the third party for pharmaceutical products;

querying the third party with a plurality of questions, that will narrow in scope until needs of the third party are identified;

correlating, by a computer hardware microprocessor, the needs of the third party to the pharmaceutical product when the pharmaceutical product meets the needs of the third party according to the defined advertising information of the pharmaceutical product and, in response to the correlating;

suggesting, the pharmaceutical product using the audio advertisement, and automatically mailing a sample of the pharmaceutical product to the third party without any interaction from the client;

suggesting other possible products available, when the pharmaceutical product does not meet the needs of the third party;

evaluating sales by region and specialty to identify other pharmaceutical products that the third party is interested in purchasing.

2. The method of claim 1, wherein the receiving of the request from the third party is achieved by calling a specific phone number.

3. The method of claim 1, wherein said audio advertisement is presented to the third party as a predetermined vocal persona.

4. A system for advertising a pharmaceutical product of a client to a third party, the system comprising one or more microprocessor components programmed to:

define advertising information of an audio advertisement for the pharmaceutical product by:

collecting information from the client to determine categorization of the pharmaceutical product according to: a type of medication, a use for at least one medical condition, an alternative use for at least one other medical condition and additional information consisting at least four of: a name of the pharmaceutical product, an alternative reason to use the pharmaceutical product, a recommended dosage of the pharmaceutical product, a recommended schedule of the pharmaceutical product, notes of the pharmaceutical product, and warnings of the pharmaceutical product identifying, based on the collected information, a length of time of the audio advertisement for the pharmaceutical product according to a per-minute advertisement price the client spends on the audio advertisement, determining when the additional information to be included in the audio advertisement exceeds the length of time of the audio advertisement according to the per-minute advertisement price, and in response to said determining, lengthening the length of time of the audio advertisement when the client raises the per-minute advertisement price in response to the additional information exceeding the length of time of the audio advertisement, and excluding the additional information when the client does not raise the audio advertisement per-minute price in response to the additional information exceeding the length of time of the audio advertisement;

receive a request from the third party for pharmaceutical products;

query the third party with a plurality of questions, that will narrow in scope until needs of the third party are identified;

correlate, the needs of the third party to the pharmaceutical product when the pharmaceutical product meets the needs of the third party according to the defined advertising information of the pharmaceutical product and, in response to the correlating;

suggest, the pharmaceutical product using the audio advertisement, and automatically mailing a sample of the pharmaceutical product to the third party without any interaction from the client;

suggest other possible products available, when the pharmaceutical product does not meet the needs of the third party;

evaluate sales by region and specialty to identify other pharmaceutical products that the third party is interested in purchasing.

5. The system of claim 4, wherein the one or more microprocessor components are further programmed to receive the request from the third party via a specific phone number.

6. The system of claim 4, wherein the one or more microprocessor components are further programmed to present said audio advertisement to the third party as a predetermined vocal persona.

7. A non-transitory computer readable storage medium for advertising a pharmaceutical product of a client to a third party, on which is recorded computer executable instructions that, when executed by a microprocessor, cause the microprocessor to execute the steps of a method comprising:

defining advertising information of an audio advertisement for the pharmaceutical product by:

collecting information from the client to determine categorization of the pharmaceutical product according to: a type of medication, a use for at least one medical condition, an alternative use for at least one other medical condition and additional information consisting at least four of: a name of the pharmaceutical product, an alternative reason to use the pharmaceutical product, a recommended dosage of the pharmaceutical product, a recommended schedule of the pharmaceutical product, notes of the pharmaceutical product, and warnings of the pharmaceutical product, identifying, based on the collected information, a length of time of the audio advertisement for the pharmaceutical product according to a per-minute advertisement price the client spends on the audio advertisement;

determining when the additional information to be included in the audio advertisement exceeds the length of time of the audio advertisement according to the per-minute advertisement price, and, in response to said determining, lengthening the length of time of the audio advertisement when the client raises the per-minute advertisement price in response to the additional information exceeding the length of time of the audio advertisement, and excluding the additional information when the client does not raise the audio advertisement per-minute price in response to the additional information exceeding the length of time of the audio advertisement;

receiving a request from the third party for pharmaceutical products;

querying the third party with a plurality of questions, that will narrow in scope until needs of the third party are identified;

correlating, the needs of the third party to the pharmaceutical product when the pharmaceutical product meets the needs of the third party according to the defined advertising information of the pharmaceutical product and, in response to the correlating;

suggesting, the pharmaceutical product using the audio advertisement, and automatically mailing a sample of the pharmaceutical product to the third party without any interaction from the client;

suggesting other possible products available, when the pharmaceutical product does not meet the needs of the third party;

evaluating sales by region and specialty to identify other pharmaceutical products that the third party is interested in purchasing.

8. The non-transitory computer readable storage medium of claim 7, wherein the microprocessor is further caused to execute the receiving of the request from the third party via a specific phone number.

9. The non-transitory computer readable storage medium of claim 7, wherein the microprocessor is further caused to execute presenting said audio advertisement to the third party as a predetermined vocal persona.

* * * * *